United States Patent
Itai et al.

(10) Patent No.: US 11,234,984 B2
(45) Date of Patent: Feb. 1, 2022

(54) SOLID DISPERSION

(71) Applicants: Shizuoka Prefectural University Corporation, Shizuoka (JP); Nippon Chemiphar Co., Ltd., Tokyo (JP)

(72) Inventors: Shigeru Itai, Shizuoka (JP); Shuji Noguchi, Shizuoka (JP); Yasunori Iwao, Shizuoka (JP); Masuharu Hirano, Misato (JP); Takashi Ohta, Misato (JP); Tomio Yamakawa, Misato (JP)

(73) Assignees: Shizuoka Prefectural University Corporation, Shizuoka (JP); Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 16/765,575

(22) PCT Filed: Nov. 28, 2018

(86) PCT No.: PCT/JP2018/043788
§ 371 (c)(1),
(2) Date: May 20, 2020

(87) PCT Pub. No.: WO2019/107412
PCT Pub. Date: Jun. 6, 2019

(65) Prior Publication Data
US 2020/0306251 A1    Oct. 1, 2020

(30) Foreign Application Priority Data
Nov. 28, 2017 (JP) .............................. JP2017-227807

(51) Int. Cl.
*A61K 31/519* (2006.01)
*A61K 9/19* (2006.01)
*A61K 47/38* (2006.01)

(52) U.S. Cl.
CPC .............. *A61K 31/519* (2013.01); *A61K 9/19* (2013.01); *A61K 47/38* (2013.01)

(58) Field of Classification Search
CPC ...... A61K 31/519; A61K 47/38; A61K 9/146; A61K 9/1623; A61K 9/19; A61K 9/2059; A61K 9/4858; C07D 513/04; A61P 19/06; A61P 43/00
See application file for complete search history.

(56) References Cited

U.S. PATENT DOCUMENTS

2007/0293512 A1* 12/2007 Yoshida ............... C07D 498/04
514/260.1
2014/0363504 A1   12/2014 Leng

FOREIGN PATENT DOCUMENTS

| EP | 2036561 A1 | 3/2009 |
| JP | 3938938 B2 | 6/2007 |
| JP | 5944514 B2 | 7/2016 |
| WO | 2005121153 A1 | 12/2005 |
| WO | 2016136727 A1 | 9/2016 |

OTHER PUBLICATIONS

K. Kawakami, Recent Progress in Physicochemical Characterization and Formulation Technologies for Poorly Soluble Drugs, CMC Publishing Co., Ltd., 2010.
H. Ueda, Importance of Solid Physical Property Evaluation in Formulation Development of Amorphous Drug, Farumashia, 2016, vol. 52, No. 5, pp. 392 to 396.
F. Tanno, Evaluation of Characteristics of Hypromellose Acetate Succinate (HPMCAS) as a Carrier for Solid Dispersion: from Study to Improve In Vitro Dissolution of Poorly Water Soluble Drugs, The Archives of Practical Pharmacy, 2013, vol. 73, No. 4, pp. 214 to 222.
W. Curatolo et al., Utility of Hydroxypropylmethylcellulose Acetate Succinate (HPMCAS) for Initiation and Maintenance of Drug Supersaturation in the GI Milieu, Pharm., Res., 2009, vol. 26, No. 6, pp. 1419 to 1431.
D. T. Friesen et al., Hydroxypropyl Methylcellulose Acetate Succinate-Based Spray-Dried Dispersions: An Overview, Mol. Pharm., 2008, vol. 5, No. 6, pp. 1003 to 1019.
D. D. Sun et al., Probing the Mechanisms of Drug Release from Amorphous Solid Dispersions in Medium-Soluble and Medium-Insoluble Carriers, J. Control. Release, 2015, vol. 211, pp. 85 to 93.
PCT Office, International Search Report issued in PCT/JP2018/043788 dated Feb. 12, 2019, 4 pages.

(Continued)

*Primary Examiner* — Sarah Pihonak
(74) *Attorney, Agent, or Firm* — Wood Herron & Evans LLP (57) ABSTRACT

The present invention relates to a solid dispersion containing a compound represented by General Formula (I):

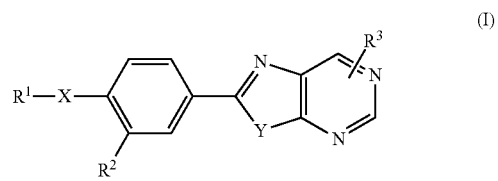

wherein $R^1$ is an unsubstituted phenyl group or a phenyl group substituted with a substituent; the substituent is an alkyl group having 1 to 8 carbon atoms, an alkyl group having 1 to 8 carbon atoms substituted with a halogen atom, an alkoxy group having 1 to 8 carbon atoms, an alkoxycarbonyl group having 2 to 8 carbon atoms, a formyl group, a carboxyl group, a halogen atom, a phenyl group or a phenoxy group; $R^2$ is a cyano group or a nitro group; $R^3$ is a hydroxyl group; X is an oxygen atom or —S(O)$_n$—; n is an integer of 0 to 2; Y is an oxygen atom or a sulfur atom, or a pharmaceutically acceptable salt thereof and a hypromellose derivative.

14 Claims, 4 Drawing Sheets

(56) References Cited

OTHER PUBLICATIONS

Liu Jing et al.: "Scale-Up Synthesis of a TRPV1 Antagonist Featuring a Facile Thiazolo [5,4-d] pyrimidine Formation," Organic Process Research and Development, vol. 15, No. 2, 2011, pp. 382-388.
European Patent Office, Search Report issued in EP 18882399.1 dated Aug. 2, 2021.

* cited by examiner

SOLID DISPERSION

TECHNICAL FIELD

The present invention relates to a solid dispersion containing a compound having a high xanthine oxidase inhibitory activity or a pharmaceutically acceptable salt thereof, and a hypromellose derivative.

Priority is claimed on Japanese Patent Application No. 2017-227807, filed Nov. 28, 2017, the content of which is incorporated herein by reference.

BACKGROUND ART

Hyperuricemia causes gout, kidney failure, and the like, and is considered to be a risk factor for coronary artery disease. It has been pointed out that hyperuricemia has a close relationship with the onset of lifestyle-related diseases such as hypertension. Therefore, the treatment of hyperuricemia includes not only treatment of gout but also prevention of various lifestyle-related diseases associated with aging.

Currently, xanthine oxidase inhibitors such as allopurinol and febuxostat are mainly used for the treatment of hyperuricemia. In addition, a compound described in PCT International Publication No. WO 2005/121153 pamphlet (Patent Literature 1) has been reported as a compound having a similar mechanism.

The inventors made a study on a compound having a high xanthine oxidase inhibitory activity disclosed in Patent Literature 1 and found that there was still room for improvement in in vivo absorbability when this compound was orally administered to a living body.

Regarding a method of improving in vivo absorbability of a poorly soluble compound, a method of micronizing a poorly soluble compound and a method of forming a solid dispersion therefrom.

For example, in Non-Patent Literature 1, a method of micronizing a compound to a nano level is disclosed. In Patent Literature 2, a method of preparing a solid dispersion in which a xanthine derivative is dispersed in a methacrylic acid copolymer is disclosed. In Patent Literature 3, a method of preparing a solid dispersion containing N4-(4-([1,2,4]triazolo[1,5-a]pyridin-7-yloxy)-3-methylphenyl)-N6-(4,4-dimethyl-4,5-dihydrooxazol-2-yl)quinazoline-4,6-diamine and a dispersion polymer is disclosed.

However, in order to improve in vivo absorbability of a poorly soluble compound by forming a solid dispersion, it is necessary to form the poorly soluble compound into an amorphous form. However, since such a poorly soluble compound may change from an amorphous form to a crystal during long-term storage depending on the combination of a poorly soluble compound and a polymer, there are problems of constant solubility not being obtained with the passage of time and the like.

CITATION LIST

Patent Documents

[Patent Literature 1]
PCT International Publication No. WO 2005/121153 pamphlet
[Patent Literature 2]
Japanese Patent No. 3938938
[Patent Literature 3]
Japanese Patent No. 5944514

Non-Patent Documents

[Non-Patent Literature 1]
Evaluation of the physical properties of poorly water-soluble drugs and new development of formulation designs, CMC Publishing, 2010, pages 141 to 150

SUMMARY OF THE INVENTION

Problems to be Solved by the Invention

Objects of the present invention are to improve in vivo absorbability of the compound disclosed in Patent Literature 1 or a pharmaceutically acceptable salt thereof, and provide a pharmaceutical composition containing them as an active ingredient.

Means to Solve the Problems

The inventors conducted various studies regarding improvement in absorbability of the compound disclosed in Patent Literature 1 or a pharmaceutically acceptable salt thereof, and as a result found that when a solid dispersion with a specific polymer was formed, in vivo absorbability and storage stability were improved, thus completing the present invention.

Specifically, the present invention provides the following aspects.

[1] A solid dispersion containing a compound represented by General Formula (I):

(I)

wherein $R^1$ is an unsubstituted phenyl group or a phenyl group substituted with a substituent, the substituent being at least one group selected from the group consisting of an alkyl group having 1 to 8 carbon atoms, an alkyl group having 1 to 8 carbon atoms substituted with a halogen atom, an alkoxy group having 1 to 8 carbon atoms, an alkoxycarbonyl group having 2 to 8 carbon atoms, a formyl group, a carboxyl group, a halogen atom, a phenyl group and a phenoxy group, $R^2$ is a cyano group or a nitro group, $R^3$ is a hydroxyl group, X is an oxygen atom or $—S(O)_n—$, n is an integer of 0 to 2, and Y is an oxygen atom or a sulfur atom) or a pharmaceutically acceptable salt thereof and a hypromellose derivative;

[2] The solid dispersion according to [1], wherein $R^1$ is an unsubstituted phenyl group or a phenyl group substituted with a halogen atom.

[3] The solid dispersion according to [1] or [2], wherein X is an oxygen atom;

[4] The solid dispersion according to any one of [1] to [3], wherein Y is a sulfur atom;

[5] The solid dispersion according to any one of [1] to [4], wherein the compound represented by General Formula (I) or a pharmaceutically acceptable salt thereof is amorphous;

[6] The solid dispersion according to any one of [1] to [5], wherein a weight ratio between the compound represented by General Formula (I) or a pharmaceutically acceptable salt thereof and a hypromellose derivative is 1:0.1 to 1:25;

[7] The solid dispersion according to any one of [1] to [6], wherein the hypromellose derivative is hypromellose acetate succinate or hypromellose phthalate;

[8] A method of producing a solid dispersion, including: producing the solid dispersion according to any one of [1] to [7] using a spray dry method;

[9] A pharmaceutical composition comprising the solid dispersion according to any one of [1] to [7]; or

[10] The pharmaceutical composition according to [9], which is a solid preparation.

Effects of the Invention

The solid dispersion of the present invention is useful as a therapeutic agent for hyperuricemia and the like because it exhibits excellent in vivo absorbability and storage stability.

EMBODIMENTS FOR CARRYING OUT THE INVENTION

The present invention will be described below in further detail.

In a compound represented by General Formula (I), $R^1$ is an unsubstituted phenyl group or a phenyl group substituted with a substituent.

Examples of "an alkyl group having 1 to 8 carbon atoms" as a substituent in the phenyl group represented by $R^1$ include a methyl group, an ethyl group, a propyl group, an isopropyl group, a butyl group, an isobutyl group, a tert-butyl group, a pentyl group, and a hexyl group, and a methyl group or an ethyl group is preferable.

Examples of "an alkyl group having 1 to 8 carbon atoms substituted with a halogen atom" as a substituent in the phenyl group represented by $R^1$ include a fluoromethyl group, a trifluoromethyl group, a 1,1-difluoroethyl group, and a pentafluoroethyl group, and a fluoromethyl group or a trifluoromethyl group is preferable.

Examples of "an alkoxy group having 1 to 8 carbon atoms" as a substituent in the phenyl group represented by $R^1$ include a methoxy group, an ethoxy group, a propoxy group, an isopropoxy group, a butoxy group, an isobutoxy group, and a tert-butoxy group, and a methoxy group is preferable.

Examples of "an alkoxycarbonyl group having 2 to 8 carbon atoms" as a substituent in the phenyl group represented by $R^1$ include a methoxycarbonyl group, an ethoxycarbonyl group, a propoxycarbonyl group, a butoxycarbonyl group, and a tert-butoxycarbonyl group, and a methoxycarbonyl group or an ethoxycarbonyl group is preferable.

Examples of a "halogen atom" as a substituent in the phenyl group represented by $R^1$ include a fluorine atom, a chlorine atom, a bromine atom, and an iodine atom, and a fluorine atom or a chlorine atom is preferable.

Regarding $R^1$, an unsubstituted phenyl group is preferable.

In the compound represented by General Formula (I), $R^2$ is a cyano group or a nitro group, and a cyano group is preferable.

In the compound represented by General Formula (I), X is an oxygen atom or —S(O)$_n$—, and an oxygen atom is preferable.

In the compound represented by General Formula (I), Y is an oxygen atom or a sulfur atom, and a sulfur atom is preferable.

Examples of the pharmaceutically acceptable salt of the compound represented by General Formula (I) include an alkali metal salt such as a sodium salt, a potassium salt, and a lithium salt, and a potassium salt is preferable.

The compound of General Formula (I) used in a solid dispersion which is one embodiment of the present invention can be obtained by, for example, a synthesis method described in Patent Literature 1.

Regarding the compound of General Formula (I) used in a solid dispersion of the present invention, compounds in Table 1 may be exemplified as preferable compounds. In the table, Me is a methyl group.

TABLE 1

| | Structural formula | Compound name |
| --- | --- | --- |
| Compound 1 |  | 2-[4-(4-Chlorophenylthio)-3-nitrophenyl]-7-hydroxy-thiazolo[5,4-d]pyrimidine |
| Compound 2 |  | 7-Hydroxy-2-(3-nitro-4-phenylthiophenyl)thiazolo[5,4-d]pyrimidine |

TABLE 1-continued

| | Structural formula | Compound name |
|---|---|---|
| Compound 3 | | 2-[4-(4-Chlorophenoxy)-3-nitrophenyl]-7-hydroxy-thiazolo[5,4-d]pyrimidine |
| Compound 4 | | 7-Hydroxy-2-(3-nitro-4-phenoxyphenyl)thiazolo[5,4-d]pyrimidine |
| Compound 5 | | 2-[4-(4-Fluorophenoxy)-3-nitrophenyl]-7-hydroxy-thiazolo[5,4-d]pyrimidine |
| Compound 6 | | 2-[4-(4-Methoxyphenoxy)-3-nitrophenyl]-7-hydroxy-thiazolo[5,4-d]pyrimidine |
| Compound 7 | | 2-[4-(3-Chlorophenoxy)-3-nitrophenyl]-7-hydroxy-thiazolo[5,4-d]pyrimidine |
| Compound 8 | | 2-[4-(2-Chlorophenoxy)-3-nitrophenyl]-7-hydroxy-thiazolo[5,4-d]pyrimidine |
| Compound 9 | | 2-[4-(3-Fluorophenoxy)-3-nitrophenyl]-7-hydroxy-thiazolo[5,4-d]pyrimidine |
| Compound 10 | | 2-[4-(2-Fluorophenoxy)-3-nitrophenyl]-7-hydroxy-thiazolo[5,4-d]pyrimidine |

TABLE 1-continued

| Structural formula | Compound name |
| --- | --- |
| Compound 11 | 7-Hydroxy-2[4-(4-methoxy-carbonylphenoxy)-3-nitrophenyl]thiazolo[5,4-d]pyrimidine |
| Compound 12 | 2-[4-(4-Fluorophenoxy)-3-nitrophenyl]-7-hydroxy-oxazolo[5,4-d]pyrimidine |
| Compound 13 | 2-[3-Cyano-4-(2-fluorophenoxy)phenyl]-7-hydroxythiazolo[5,4-d]pyrimidine |
| Compound 14 | 2-(3-Cyano-4-phenoxyphenyl)-7-hydroxythiazolo[5,4-d]pyrimidine |

The pharmaceutically acceptable salt may be formed from Compound 1 to Compound 14. Among these, Compound 3 to Compound 5, Compound 8 to Compound 10, Compound 13 to Compound 14, or a pharmaceutically acceptable salt of these compounds are preferable.

"A hypromellose derivative" according to the present invention represents hypromellose itself (may be abbreviated as HPMC), and an organic acid ester of hypromellose. Hypromellose is called hydroxypropyl methylcellulose, and is a mixed methyl group and hydroxypropyl group ether of cellulose. Examples of an organic acid forming an ester with hypromellose include acetic acid, succinic acid, and phthalic acid. Hypromellose according to the present invention may form an ester with one, two or more organic acids selected from among these organic acids.

Examples of the hypromellose derivative used in the present invention include hypromellose, hypromellose acetate succinate (may be abbreviated as HPMCAS), and hypromellose phthalate (may be abbreviated as HPMCP), and hypromellose acetate succinate or a hypromellose phthalate is preferable.

Examples of the hypromellose according to the present invention include hypromellose in which a substitution proportion per monomer unit is 28 to 30% for a methoxy group and 7 to 12% for a hydroxypropoxy group.

Examples of the hypromellose acetate succinate according to the present invention include hypromellose acetate succinates in which a substitution proportion per monomer unit is 20 to 26% and preferably 21 to 25% for a methoxy group, is 5 to 10% and preferably 5 to 9% for a hydroxypropoxyl group, is 5 to 14% and preferably 7 to 11% for an acetyl group, and is 4 to 18% and preferably 10 to 14% for a succinoyl group.

Examples of the hypromellose phthalate according to the present invention include hypromellose phthalate in which a substitution proportion per monomer unit is 18 to 24% for a methoxy group, 5 to 10% for a hydroxypropoxy group, and 21 to 35% for a carboxybenzoyl group.

A content of a methoxy group, a hydroxypropoxy group, an acetyl group, a succinoyl group, a carboxybenzoyl group, or the like in the hypromellose derivative can be measured by a method according to a method of measuring a degree of substitution of hypromellose, hypromellose acetate succinate and hypromellose phthalate defined in the 17th revised Japanese Pharmacopoeia.

A viscosity of the hypromellose derivative according to the present invention is not particularly limited as long as the effect of the present invention is obtained, for example, 2.4 to 204 mPa·s, and preferably 2.4 to 3.6 mPa·s can be mentioned.

A viscosity of the hypromellose derivative according to the present invention can be measured by a method according to a method of measuring a viscosity of hypromellose, hypromellose acetate succinate, and hypromellose phthalate defined in the 17th revised Japanese Pharmacopoeia.

A weight ratio between the compound represented by General Formula (I) or a pharmaceutically acceptable salt thereof and the hypromellose derivative can be appropriately adjusted in a range of 1:0.1 to 1:25. The weight ratio between the compound represented by General Formula (I) or a pharmaceutically acceptable salt thereof and the hypromellose derivative is 1:0.1 to 1:10 in one aspect, 1:0.1 to 1:4 in another aspect, 1:1 to 1:10 in still another aspect, 1:2 to 1:5 in yet another aspect, and 1:3 to 1:4 in yet another aspect.

A solid dispersion having a weight ratio between 2-(3-cyano-4-phenoxyphenyl)-7-hydroxythiazolo[5,4-d]pyrimidine or a pharmaceutically acceptable salt thereof and the hypromellose derivative of 1:0.1 to 1:25 in one embodiment of the present invention, 1:0.1 to 1:10 in another embodiment, 1:0.1 to 1:4 in still another embodiment, 1:1 to 1:10 in yet another embodiment, 1:2 to 1:5 in yet another embodiment, and 1:3 to 1:4 in yet another embodiment, can be mentioned.

The term "solid dispersion" refers to a solid system containing at least two components, and a solid composition forming a system in which at least two components are uniformly mixed together. In addition, in the solid dispersion, at least one component is generally dispersed throughout the system.

Therefore, one aspect of the "solid dispersion" of the present invention is a solid composition which contains the compound represented by General Formula (I) or a pharmaceutically acceptable salt thereof and the hypromellose derivative, and forms a system in which the compound represented by General Formula (I) or a pharmaceutically acceptable salt thereof and the hypromellose derivative are uniformly mixed together.

Another aspect of the "solid dispersion" of the present invention is a solid composition forming a system in which the compound represented by General Formula (I) or a pharmaceutically acceptable salt thereof are dispersed throughout the hypromellose derivative. In this case, the compound represented by General Formula (I) or a pharmaceutically acceptable salt thereof forms a dispersed phase as a dispersoid, and the hypromellose derivative forms a continuous phase as a dispersion medium.

The "solid dispersion" of the present invention is composed of the compound represented by General Formula (I) or a pharmaceutically acceptable salt thereof, the hypromellose derivative, and optionally a pharmaceutically acceptable additive. Examples of the pharmaceutically acceptable additive optionally contained include the additive selected from among a surfactant, a pH-adjusting agent, sugars and a plasticizer. These can be appropriately combined and added to a solid dispersion of the present invention in required amounts.

Examples of the surfactant that can be used include a cationic surfactant such as sodium bis-(2-ethylhexyl)sulfosuccinate (sodium docusate), and an alkyltrimethylammonium bromide (for example, cetyltrimethylammonium bromide (cetrimide)), an anionic surfactant such as sodium lauryl sulfate, and a nonionic surfactant such as polyoxyethylene sorbitan (for example, Tween (Tween™ 20, 40, 60, 80 or 85)), and a sorbitan fatty acid ester (for example, Span™ 20, 40, 60, 80, or 85).

Examples of the pH-adjusting agent that can be used include an acid such as succinic acid, maleic acid, tartaric acid, citric acid, and aspartic acid, and an alkali such as sodium hydroxide, magnesium oxide, silicon dioxide, sodium hydrogen carbonate, and L-arginine.

Examples of the sugar that can be used include lactose, white sugar, glucose, fructose, sucrose, maltose (malt sugar), reduced maltose, maltitol, mannitol, erythritol, sorbitol, and xylitol.

Examples of the plasticizer that can be used include triethyl citrate, polyethylene glycol, and triacetin.

The "solid dispersion" of the present invention may not contain a pharmaceutically acceptable additive. However, when a pharmaceutically acceptable additive is contained, for example, a weight ratio between the compound represented by General Formula (I) or a pharmaceutically acceptable salt thereof and the surfactant is 1:0.01 to 1:2, more preferably 1:0.02 to 1:1.5, and most preferably 1:0.03 to 1:1.2, a weight ratio between the compound represented by General Formula (I) or a pharmaceutically acceptable salt thereof and the pH-adjusting agent is 1:0.01 to 1:2, more preferably 1:0.02 to 1:1.5, and most preferably 1:0.03 to 1:1.2, a weight ratio between the compound represented by General Formula (I) or a pharmaceutically acceptable salt thereof and the sugar is 1:0.02 to 1:20, and more preferably 1:0.15 to 1:10, and a weight ratio between the compound represented by General Formula (I) or a pharmaceutically acceptable salt thereof and the plasticizer is 1:0.02 to 1:20, and more preferably 1:0.15 to 1:10.

In the "solid dispersion" of the present invention, the pharmaceutically acceptable additive may constitute a dispersed phase or a continuous phase of the solid dispersion.

In the "solid dispersion" of the present invention, it is preferable that a part or all of the compound represented by General Formula (I) or a pharmaceutically acceptable salt thereof be amorphous. Here, the term "amorphous" means that a substance has a form having a short-distance order between atoms or molecules of the compound represented by General Formula (I) or a pharmaceutically acceptable salt thereof and having no long-distance order such as in crystals.

In the present invention, an amorphous state can be identified according to a halo peak shown in X-ray diffraction.

In the present invention, with respect to a total weight of the compound represented by General Formula (I) or a pharmaceutically acceptable salt thereof, an amorphous content is preferably 50 weight % or more, more preferably 80 weight % or more, still more preferably 90 weight % or more, yet more preferably 95 weight % or more, yet more preferably 98 weight % or more, and an amorphous content may be 100 weight %. The amorphous content can be obtained by an X-ray diffraction method.

The solid dispersion of the present invention can be produced by a method known per se. For example, a mixing and grinding method (a mechano-chemical method), a solvent method, a melting method, a hot melt extrusion method, and the like can be used for production.

Here, in the mixing and grinding method, the compound represented by General Formula (I) or a pharmaceutically acceptable salt thereof and the hypromellose derivative, and optionally a pharmaceutically acceptable additive are mixed together, and a conventional method using a mixer and a grinding machine such as a ball mill and a hammer mill, can be then performed.

The solvent method refers to a method in which the compound represented by General Formula (I) or a pharmaceutically acceptable salt thereof and the hypromellose derivative, and optionally a pharmaceutically acceptable additive are dissolved or suspended in a solvent (an organic solvent, water or a mixed solution thereof), and the solvent is then removed to precipitate a solid dispersion or a solid dispersion is precipitated in the solvent.

The solvent can be removed by a method such as spray methods (can be classified into a fluid bed method, a blowing drying method (also called a spray dry method), a rolling layer method, a stirring method, a supercritical method or the like according to an embodiment), a filtration method, an evaporation method, a freeze-drying method, or the like. A spray method is preferable, and a spray-drying method is particularly preferable among these methods.

Regarding the solvent that can be used to produce the solid dispersion of the present invention, a pharmaceutically acceptable solvent is preferable. For example, ethanol, methanol, 2-propanol, acetone, 2-butanone, methyl isobutyl ketone, tetrahydrofuran (THF), tetrahydropyran, 1,4-dioxane, diethyl ether, toluene, acetonitrile, methylene chloride, chloroform, methyl acetate, ethyl acetate, butyl acetate, acetic acid, formic acid, N,N-dimethylformamide, N,N-dimethylacetamide, and dimethyl sulfoxide may be used.

It is preferable that the compound represented by General Formula (I) or a pharmaceutically acceptable salt thereof and a pharmaceutically acceptable additive optionally added dissolve in such a solvent.

In the spray-drying method, the solid dispersion can be produced by a method known per se. For example, the compound represented by General Formula (I) or a pharmaceutically acceptable salt thereof and the hypromellose derivative, and optionally a pharmaceutically acceptable additive may be added to the solvent to prepare a solution or suspension, the solution or suspension may be formed into a fine mist by centrifugal spraying using a rotating disk or pressure spraying using a pressure nozzle, and this may be sprayed into a drying medium (heated air or nitrogen gas), and thereby a solid dispersion can be obtained as a powdered dried component.

In the spray-drying method, the temperature of the drying medium is, for example, 50 to 120° C., and preferably 50 to 90° C. The drying medium may be caused to flow in a certain direction, and can be caused to flow as an air flow, for example, at 0.2 to 0.6 m$^3$/min, and preferably 0.3 to 0.5 m$^3$/min.

The precipitation method in the solvent methods is preferably a coprecipitation method, and the compound represented by General Formula (I) or a pharmaceutically acceptable salt thereof and the hypromellose derivative, and optionally a pharmaceutically acceptable additive are dissolved or suspended in a solvent, the dissolved compound (I) or the pharmaceutically acceptable salt, and the hypromellose derivative, and the pharmaceutically acceptable additive optionally added are precipitated by lowering the dissolution concentration by addition of an insoluble solvent, lowering a temperature, or the like, and thereby a solid dispersion can be obtained.

The melting method is a method in which the compound represented by General Formula (I) or a pharmaceutically acceptable salt thereof and the hypromellose derivative, and optionally a pharmaceutically acceptable additive are heated to the melting point or the softening point of hypromellose derivatives or higher and stirred, and thus the compound represented by General Formula (I) or the pharmaceutically acceptable salt thereof and the pharmaceutically acceptable additive optionally added are dissolved or dispersed in the hypromellose derivative and then rapidly cooled. In this case, optionally an additive, for example, a plasticizer such as triethyl citrate, polyethylene glycol, and triacetin, and a surfactant can be additionally added. The production can be performed using a stirring granulator having a heating device.

The hot melt extrusion method is a method in which the compound represented by General Formula (I) or a pharmaceutically acceptable salt thereof and the hypromellose derivative, and optionally a pharmaceutically acceptable additive are heated and mixed under pressure using an extruder having a heating device, for example, a 2-screw extruder, and thereby a solid dispersion is obtained. The obtained plastic-like solid dispersion can be ground using a grinding machine to obtain a solid dispersion powder.

The solid dispersion of the present invention produced according to the above production method can be formed into solid dispersion particles having a certain particle size by a known method, and the solid dispersion particles can be directly used as a powder or a granular agent.

A pharmaceutical composition containing the solid dispersion of the present invention contains the solid dispersion and a pharmaceutically acceptable additive. Regarding the pharmaceutically acceptable additive, for example, a binding agent, a disintegrating agent, a diluting agent, a lubricant, and the like are appropriately combined and added in required amounts, and thereby a pharmaceutical composition of the present invention can be produced.

Examples of the binding agent that can be used in the pharmaceutical composition of the present invention include methyl cellulose, hydroxyethyl cellulose, hydroxypropyl cellulose, hypromellose, polyvinyl pyrrolidone, gelatin, agar, alginic acid, sodium alginate, partially saponified polyvinyl alcohol, pullulan, partly pregelatinized starch, dextrins, xanthan gum, and gum arabic powder, and hydroxypropyl cellulose, hypromellose, or polyvinyl pyrrolidone is preferable. These may be used alone or two or more types thereof may be used in combination.

Examples of the disintegrating agent that can be used in the pharmaceutical composition of the present invention include crystalline cellulose, carboxymethyl cellulose (carmellose), croscarmellose sodium, calcium carboxymethyl cellulose, low-substituted hydroxypropyl cellulose, crospovidone, hydroxypropyl starch, starch, partly pregelatinized starch, and starch sodium glycolate. Croscarmellose sodium, starch sodium glycolate, and crospovidone are preferable, and crospovidone is more preferable. An amount of the disintegrating agent added is preferably 5 to 30 weight % and more preferably 5 to 15 weight % with respect to a total weight of the pharmaceutical composition. In addition, when formulated into tablets, an amount of the disintegrating agent added is preferably 1 to 10 weight % and more preferably 2 to 6 weight % in granules for tableting.

The diluting agent that can be used in the pharmaceutical composition of the present invention can be added to a kneaded product, a granulated product or after the granulation. Examples of the diluting agent include celluloses such as crystalline cellulose, ethyl cellulose, hydroxypropyl cellulose, low-substituted hydroxypropyl cellulose, hydroxypropyl methylcellulose (hypromellose, etc.), starches such as corn starch, potato starch, wheat starch, rice starch, partly pregelatinized starch, and hydroxypropyl starch, sugars such as glucose, lactose, white sugar, refined white sugar, powdered sugar, trehalose, dextran, and dextrins, sugar alcohols such as D-mannitol, xylitol, sorbitol, and erythritol, glycerin fatty acid esters, inorganic salts such as magnesium aluminometasilicate, synthetic hydrotalcite, anhydrous calcium phosphate, precipitated calcium carbonate, calcium silicate, calcium hydrogen phosphate hydrate, and sodium hydrogen carbonate, and crystalline cellulose is preferable.

Examples of the lubricant that can be used in the pharmaceutical composition of the present invention include stearic acid, sodium stearyl fumarate, magnesium stearate, calcium stearate, sucrose fatty acid ester, polyethylene glycol, light anhydrous silicic acid, hardened oils, glycerin fatty acid esters, and a talc. Sodium stearyl fumarate, magnesium stearate, calcium stearate, and sucrose fatty acid esters are preferable. These may be used alone or two or more types thereof may be used in combination.

The pharmaceutical composition of the present invention is subjected to a formulation process known per se and formulated into and provided as a solid preparation such as a tablet, a capsule, a granular agent, a powder, and a trochiscus or a liquid preparation such as an injection product. Here, regarding the injection product, the pharmaceutical composition of the present invention may be provided as a solid preparation, put into the injection product for use, and used.

Since the present invention has an effect of preventing tableting failures, it is particularly preferable when the solid preparation has a tablet form. In addition, such a solid preparation can be optionally coated.

A content of the solid dispersion in the pharmaceutical composition of the present invention is 10 to 95 weight %, preferably 30 to 90 weight %, and more preferably 60 to 85 weight % with respect to a total weight of the pharmaceutical composition.

The solid dispersion of the present invention or the pharmaceutical composition containing the solid dispersion can be orally or parenterally administered to humans or other mammals, and is useful as a therapeutic agent for hyperuricemia or gout. The term "treatment" in this specification may include the concept of prophylactic or prophylactic use in addition to treatment.

One aspect of the present invention is a method of treating hyperuricemia or gout including administering a therapeutically effective amount of the solid dispersion of the present invention or the pharmaceutical composition containing the solid dispersion to a subject for which a hyperuricenmia or gout treatment is necessary.

Another aspect of the present invention is the solid dispersion of the present invention or the pharmaceutical composition containing the solid dispersion for use in treatment of hyperuricemia or gout.

Still another aspect of the present invention is use of the solid dispersion of the present invention for producing a therapeutic agent for hyperuricemia or gout.

A dose of the solid dispersion of the present invention or the pharmaceutical composition containing the solid dispersion can be adjusted according to a content of the compound represented by General Formula (I) or a pharmaceutically acceptable salt thereof in the solid dispersion of the present invention or the pharmaceutical composition containing the solid dispersion. In addition, the dose can be appropriately determined according to an administering method, and age, body weight, gender, symptoms and sensitivity to a drug of an administering subject, and the like, but it may be adjusted according to the progress of improvement in symptoms.

A dose of the solid dispersion of the present invention or the pharmaceutical composition containing the solid dispersion, for example, in terms of a content of the compound represented by General Formula (I) or a pharmaceutically acceptable salt thereof for adults, of about 0.1 mg to 100 mg per day for an injection product and 1 mg to 2000 mg per day for oral administration can be usually administered, but it can be increased or decreased according to age, symptoms, and the like. In addition, the number of administrations is, for example, 1 to 3 times per day, and preferably 1 to 2 times.

EXAMPLES

The present invention will be described below in further detail with reference to examples, comparative examples, and test examples, but the present invention is not limited thereto.

Example 1 and Comparative Examples 1 to 9.
Production of Solid Dispersions (Polymer, 25-Fold Amount)

250 mg of 2-(3-cyano-4-phenoxyphenyl)-7-hydroxythiazolo[5,4-d]pyrimidine (hereinafter referred to as a compound A in some cases) was dissolved in tetrahydrofuran to prepare a 100 mL solution. To 125 mg of each of polymers shown in Table 2, 5 mL of the mixed solution (dichloromethane/methanol=50/15) was added and dissolved. 2 mL of the solution containing the compound A was put into a test tube, and 5 mL of the polymer solution was added thereto and mixed in a vortex mixer to prepare a uniform mixture. In addition, a sample to which no polymer was added was also prepared (Comparative Example 9). A nitrogen gas stream was blown to this sample, and thereby the solvent was distilled off. Then, drying was performed under a reduced pressure overnight and thereby a solid dispersion sample containing the compound A was obtained.

HPMCAS used in Example 1 was of an MF type (specifically, regarding a substitution proportion per monomer unit, a methoxy group: 21.0 to 25.0%, a hydroxypropoxy group: 5.0 to 9.0%, and an acetyl group: 7.0 to 11.0%, and a succinoyl group: 10.0 to 14.0%, and a viscosity: 2.4 to 3.6 mPa·s).

TABLE 2

| | Polymer | Type | Polymer weight ratio | Manufacturer |
|---|---|---|---|---|
| Example 1 | HPMCAS | MF | 25-fold amount | Shin-Etsu Chemical Co., Ltd. |
| Comparative Example 1 | HPMC | TC-5 ® | 25-fold amount | Shin-Etsu Chemical Co., Ltd. |
| Comparative Example 2 | Eudragit | S-100 | 25-fold amount | Evonik Degussa Japan Co., Ltd. |
| Comparative Example 3 | Eudragit | E-100 | 25-fold amount | Evonik Degussa Japan Co., Ltd. |
| Comparative Example 4 | Eudragit | L-100 | 25-fold amount | Evonik Degussa Japan Co., Ltd. |
| Comparative Example 5 | PVP | Kollidon ®25 | 25-fold amount | BASF Japan Ltd. |
| Comparative Example 6 | PEG | 6000 | 25-fold amount | Wako Pure Chemical Corporation |
| Comparative Example 7 | Crospovidone | Kollidon CL-M | 25-fold amount | BASF Japan Ltd. |

TABLE 2-continued

| | Polymer | Type | Polymer weight ratio | Manufacturer |
|---|---|---|---|---|
| Comparative Example 8 | Poloxamer 188 | P188 | 25-fold amount | BASF Japan Ltd. |
| Comparative Example 9 | None | — | — | — |

Test Example 1. Solubility Test 5 mL of a first fluid (pH1.2) or 5 mL of a first fluid (pH6.8) for an elution test in Japanese Pharmacopoeia was added to the solid dispersions of Example 1 and Comparative Examples 1 to 8, and the sample of Comparative Example 9, the solid dispersions were ground using a glass rod or a spatula, and then shaken at 37° C. for 2 hours. 400 µL of a mixed solution (acetonitrile/water=3/2) was immediately added to 600 µL of the sample solution filtered off using a 0.45 µm filter, and a concentration of the compound A in the sample solution was measured by HPLC (Shimadzu Corporation). The results are shown in Table 3. Here, values in the table are the mean values obtained by repeating measurements twice.

TABLE 3

| | Sample | Solubility of Compound A (µg/mL) |
|---|---|---|
| First fluid for dissolution test | Comparative Example 3 | 121 |
| | Comparative Example 9 | 0.39 |
| Second fluid for dissolution test | Example 1 | 44.6 |
| | Comparative Example 4 | 7.32 |
| | Comparative Example 9 | 0.49 |

The solubility of the compound A in Comparative Example 9 was 0.39 µg/mL in the first fluid, and 0.49 µg/mL in the first fluid. However, in Example 1, and Comparative Examples 3 and 4, the solubility increased to 5.0 µg/mL or more. In particular, Eudragit E-100 as a basic polymer in Comparative Example 3 in the first fluid under acidic conditions, and HPMCAS as an acidic polymer of Example 1 in the first fluid under neutral conditions had a strong effect of improving the solubility of the compound A.

Example 2, Comparative Examples 10 and 11. Production of Solid Dispersions (Polymer, 25-Fold Amount)

The compound A was dissolved in tetrahydrofuran and adjusted to 2.5 mg/mL solution. Polymers shown in Table 4 were dissolved in a mixed solvent (methanol/dichloromethane=3/4) and adjusted to about 45 mg/mL. The solution containing the compound A was added to the polymer solution while stirring so that a weight ratio between the compound A and the polymer was 1:25. In addition, a sample to which no polymer was added was also prepared. The solution was immediately transferred into an eggplant flask, and the organic solvent was distilled off using a rotary evaporator (N-1100, Tokyo Rikakikai Co., Ltd.). The eggplant flask was transferred to a desiccator, and dried under a reduced pressure for about 16 hours using a vacuum pump, and thereby a solid dispersion containing the compound A was obtained. The solid dispersion was dried, then ground using an agate mortar or ground using a portable high-speed grinder (LM-PLUS, Osaka Chemical Co., Ltd.), and then sieved (a sieve opening: 150 µm).

TABLE 4

| | Polymer | Type | Polymer weight ratio | Manufacturer |
|---|---|---|---|---|
| Example 2 | HPMCAS | MF | 25-fold amount | Shin-Etsu Chemical Co., Ltd. |
| Comparative Example 10 | Eudragit | E-100 | 25-fold amount | Evonik Degussa Japan Co., Ltd. |
| Comparative Example 11 | None | — | — | — |

Test Example 2. Absorbability of the Solid Dispersion Containing the Compound A in Rats A single dose of 10 mg/kg or 30 mg/kg, as the compound A, of the solid dispersions of Example 2 and Comparative Example 10, and the sample of Comparative Example 11 suspended in a 1% carboxymethylcellulose aqueous solution was orally administered to fasted male rats (8 weeks old, Crl:CD (SD), Japan Charles River Laboratories). A crystalline form of the compound A was used as a control (Comparative Example 12). A collection time was 0.5, 1, 2, 4, 8, and 24 hours after administration, and about 300 µL of blood was collected at each time point from vena caudalis (n=3). The obtained blood was centrifuged at 1500×g, 4° C. for 15 minutes to obtain a plasma. The concentration of the compound A in the plasma was measured by HPLC (Shiseido and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 5. Here, values in the table are the mean value±standard deviation of three examples.

The solid dispersions of Example 2 and Comparative Example 10, and the sample of Comparative Example 11 exhibited higher absorption-improving effect on $C_{max}$ and AUC than those of the drug substance. Therefore, when the compound A was prepared in an amorphous form and in a solid dispersion form, improvement in the absorbability was exhibited. In addition, the solid dispersion with HPMCAS exhibited a stronger absorption-improving effect than the solid dispersion with Eudragit.

TABLE 5

| | Dose (mg/kg) | $T_{max}$ (hr) | $C_{max}$ (ng/mL) | $AUC_{last}$ (ng · hr/mL) |
|---|---|---|---|---|
| Example 2 | 10 | 2.7 ± 1.2 | 3010 ± 228 | 16416 ± 2792 |
| Example 2 | 30 | 4.0 ± 3.5 | 5373 ± 587 | 63160 ± 27388 |
| Comparative Example 10 | 10 | 4.0 ± 0.0 | 1936 ± 1246 | 9422 ± 5470 |

TABLE 5-continued

|  | Dose (mg/kg) | $T_{max}$ (hr) | $C_{max}$ (ng/mL) | $AUC_{last}$ (ng · hr/mL) |
|---|---|---|---|---|
| Comparative Example 10 | 30 | 8.0 ± 0.0 | 1611 ± 284 | 15120 ± 12187 |
| Comparative Example 11 | 30 | 3.7 ± 3.8 | 1724 ± 65 | 15369 ± 7776 |
| Comparative Example 12 | 30 | 4.7 ± 3.1 | 239 ± 99 | 1157 ± 261 |

$AUC_{last}$: an area under the plasma concentration-time curve up to the final observation point

Examples 3, 4 and 5. Production of Solid Dispersions (Polymer, 25-Fold Amount)

The compound A was dissolved in tetrahydrofuran and adjusted to 2.5 mg/mL. Polymers shown in Table 6 were dissolved in a mixed solvent (methanol/dichloromethane=3/4) and adjusted to about 45 mg/mL. Mixing was performed so that a weight ratio between the compound A and the polymer was 1:25, and then the solvent was distilled off using a rotary evaporator (N-1100, Tokyo Rikakikai Co., Ltd.) under a reduced pressure at about 50° C. The obtained primary dried component was additionally subjected to secondary drying (room temperature/overnight) using a vacuum pump, the secondary dried component was appropriately ground using a portable high-speed grinder (LM-PLUS, Osaka Chemical Co., Ltd.), and then sieved (sieve opening: 300 μm).

HPMCAS used in Example 3 was of an LG type (specifically, regarding a substitution proportion per monomer unit, a methoxy group: 20.0 to 24.0%, a hydroxypropoxyl group: 5.0 to 9.0%, an acetyl group: 5.0 to 9.0%, and a succinoyl group: 14.0 to 18.0%, and a viscosity: 2.4 to 3.6 mPa·s).

HPMCAS used in Example 4 was of an MG type (specifically, regarding a substitution proportion per monomer unit, a methoxy group: 21.0 to 25.0%, a hydroxypropoxyl group: 5.0 to 9.0%, an acetyl group: 7.0 to 11.0%, and a succinoyl group: 10.0 to 14.0%, and a viscosity: 2.4 to 3.6 mPa·s).

HPMCAS used in Example 5 was of an HG type (specifically, regarding a substitution proportion per monomer unit, a methoxy group: 22.0 to 26.0%, a hydroxypropoxyl group: 6.0 to 10.0%, an acetyl group: 10.0 to 14.0%, and a succinoyl group: 4.0 to 8.0%, and a viscosity: 2.4 to 3.6 mPa·s).

TABLE 6

|  | Polymer | Type | Polymer weight ratio | Manufacturer |
|---|---|---|---|---|
| Example 3 | HPMCAS | LG | 25-fold amount | Shin-Etsu Chemical Co., Ltd. |
| Example 4 | HPMCAS | MG | 25-fold amount | Shin-Etsu Chemical Co., Ltd. |
| Example 5 | HPMCAS | HG | 25-fold amount | Shin-Etsu Chemical Co., Ltd. |

Test Example 3. Absorbability of the Solid Dispersion Containing the Compound A in Rats A single dose of 10 mg/kg, as the compound A, of the solid dispersions of Example 3, Example 4, and Example 5 suspended in a 1% carboxymethylcellulose aqueous solution was orally administered to fasted male rats (7 to 9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of the compound A in the plasma was measured by HPLC (Shiseido and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 7. Here, values in the table are the mean value±standard deviation of three examples.

In the solid dispersion of Example 4, $C_{max}$ and AUC exhibited the highest concentration in the plasma.

TABLE 7

|  | Type | Dose (mg/kg) | $T_{max}$ (hr) | $C_{max}$ (ng/mL) | $AUC_{last}$ (ng · hr/mL) |
|---|---|---|---|---|---|
| Example 3 | LG | 10 | 3.3 ± 1.2 | 3089 ± 532 | 16342 ± 2494 |
| Example 4 | MG | 10 | 3.3 ± 1.2 | 3961 ± 943 | 24039 ± 6189 |
| Example 5 | HG | 10 | 2.3 ± 1.5 | 1836 ± 112 | 8970 ± 2058 |

$AUC_{last}$: an area under the plasma concentration-time curve up to the final observation point

Examples 6 to 12. Production of Solid Dispersions (HPMCAS-MG, 1 to 10-Fold Amount)

The compound A was dissolved in tetrahydrofuran and adjusted to 2.5 mg/mL. HPMCAS-MG was dissolved in a mixed solvent (ethanol/water=4/1) and adjusted to about 45 mg/mL. Mixing was performed so that a weight ratio between the compound A and the polymer shown in Table 8 was 1:1 to 1:10. Then, the mixture was pumped into a spray dryer (GB22, Yamato Scientific Co., Ltd.) at a rate of about 5 mL/min via a peristaltic pump, and spray drying and granulation were started from a 2-fluid nozzle (with a diameter of 406 or 508 μm) at an inlet temperature of 80° C. and an outlet temperature of about 60° C. under conditions of a dry air flow of 0.32 to 0.47 m³/min and a nozzle spray air pressure of 1.0 to 3.1 kgf/cm². The obtained primary dried component was additionally subjected to secondary drying (room temperature/overnight or room temperature/overnight at 40° C./day) using a vacuum pump and sieved (sieve opening: 300 μm).

TABLE 8

|  | Polymer | Type | Polymer weight ratio | Manufacturer |
|---|---|---|---|---|
| Example 6 | HPMCAS | MG | 1-fold amount | Shin-Etsu Chemical Co., Ltd. |
| Example 7 | HPMCAS | MG | 2-fold amount | Shin-Etsu Chemical Co., Ltd. |
| Example 8 | HPMCAS | MG | 3-fold amount | Shin-Etsu Chemical Co., Ltd. |
| Example 9 | HPMCAS | MG | 3.5-fold amount | Shin-Etsu Chemical Co., Ltd. |
| Example 10 | HPMCAS | MG | 4-fold amount | Shin-Etsu Chemical Co., Ltd. |
| Example 11 | HPMCAS | MG | 5-fold amount | Shin-Etsu Chemical Co., Ltd. |
| Example 12 | HPMCAS | MG | 10-fold amount | Shin-Etsu Chemical Co., Ltd. |

Test Example 4. Absorbability of the Solid Dispersion Containing the Compound A in Rats A single dose of 10 mg/kg, as the compound A, of the solid dispersions of Examples 6 to 8, and 10 to 12 suspended in a 1% carboxymethylcellulose aqueous solution was orally administered to fasted male rats (7-9 weeks old, Crl:CD (SD), Japan Charles River Laboratories). A collection time was 0.5, 1, 2, 4, 8, and 24 hours after administration, and about 300 µL of blood was collected at each time point from vena caudalis (n=3). The obtained blood was centrifuged at 1500×g, 4° C. for 15 minutes to obtain a plasma. The concentration of the compound A in the plasma was measured by HPLC (Shiseido and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 9. Here, values in the table are the mean value±standard deviation of three examples.

In the solid dispersions of Examples 6 to 8, and 10 to 12, the concentration in the plasma increased depending on the weight ratio when a weight ratio of HPMCAS-MG with respect to the compound A was 1, 2, and 3-fold, but, in the range of a weight ratio of 3, 4, 5 and 10-fold, differences in the concentration in the plasma dependent on the weight ratio were not observed.

Figure 1:
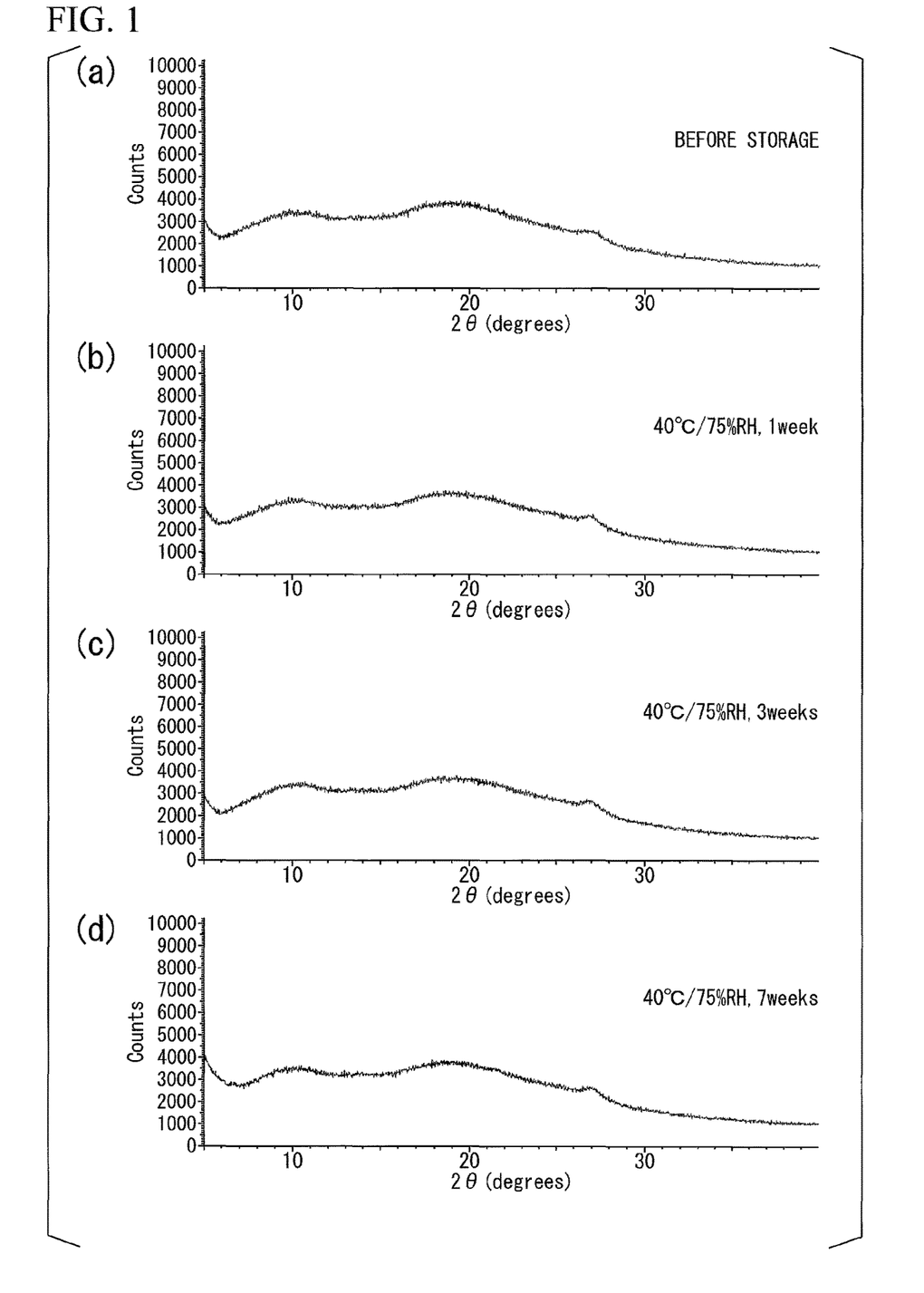
FIG. 1 shows diagrams of powder X-ray diffraction patterns of a solid dispersion of Example 9 before storage, and after 1 week, 3 weeks, and 7 weeks storage under open conditions at 40° C./75% RH, respectively.
Figure 2:
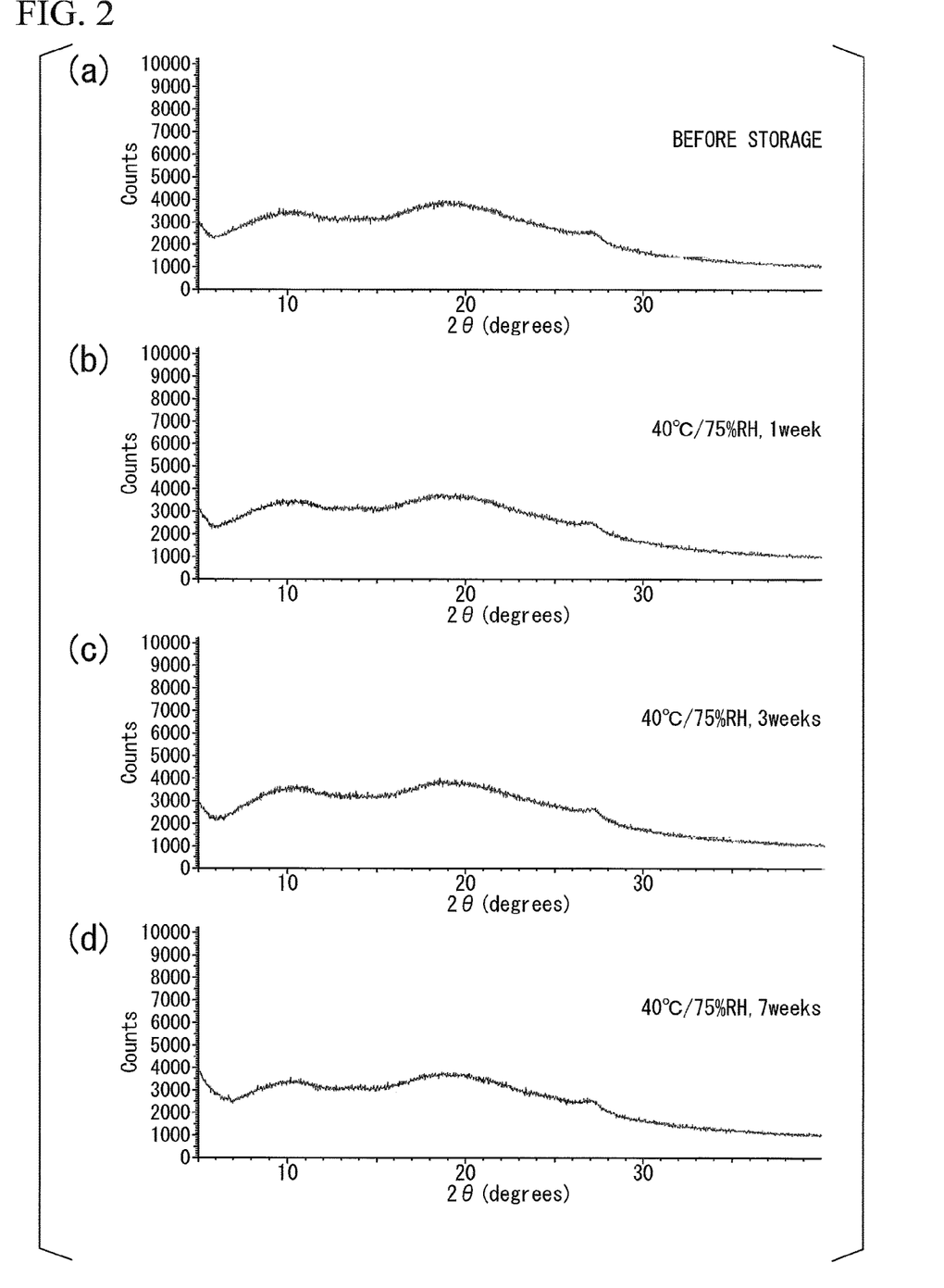
FIG. 2 shows diagrams of powder X-ray diffraction patterns of a solid dispersion of Example 10 before storage, and after 1 week, 3 weeks, and 7 weeks storage under open conditions at 40° C./75% RH, respectively.
Figure 3:
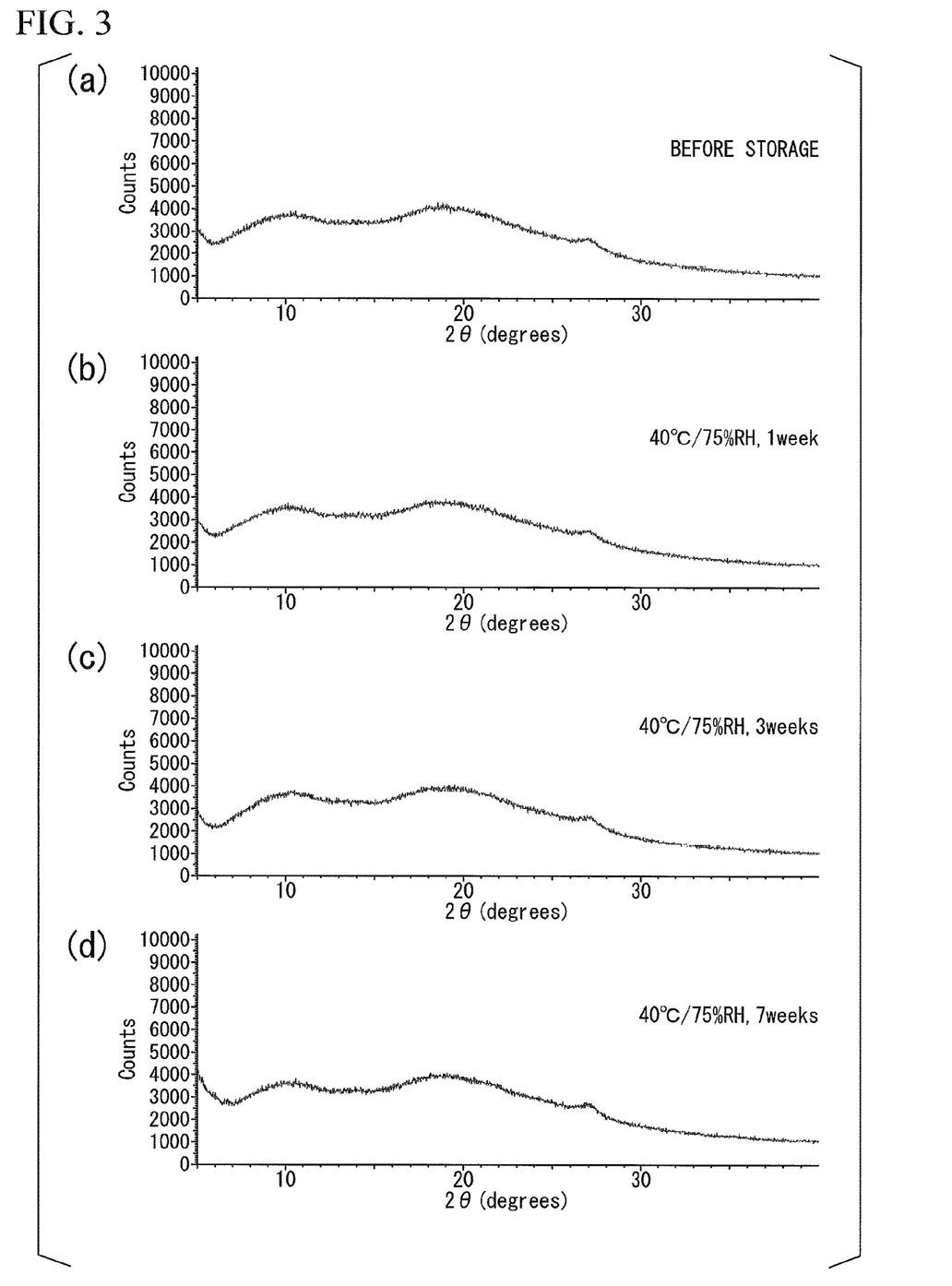
FIG. 3 shows diagrams of powder X-ray diffraction patterns of a solid dispersion of Example 11 before storage, and after 1 week, 3 weeks, and 7 weeks storage under open conditions at 40° C./75% RH, respectively.

When the solid dispersions of Examples 9 to 11 were stored under open conditions at 40° C./75% RH, changes in the powder X-ray diffraction pattern over time were not observed during storage for 7 weeks.

Test Example 6. Evaluation of the Amorphous State of the Solid Dispersion Containing the Compound A (Absorbability in Rats)

The solid dispersions of Examples 9 to 11 were stored under open conditions at 40° C./75% RH, and a change in the amorphous state was evaluated according to absorbability in rats.

A single dose of 10, and 30 mg/kg, as the compound A, of the solid dispersions of Examples 9 to 11 suspended in a 1% carboxymethylcellulose aqueous solution was orally administered to fasted male rats (7-9 weeks old, Crl:CD (SD), Japan Charles River Laboratories). A collection time was 0.5, 1, 2, 4, 8, and 24 hours after administration, and about 300 µL of blood was collected at each time point from vena caudalis (n=3). The obtained blood was centrifuged at 1500×g, 4° C. for 15 minutes to obtain a plasma. The concentration of the compound A in the plasma was measured by HPLC (Shiseido and Hitachi High-Technologies Corporation). A time to reach the highest concentration in the plasma ($T_{max}$), the highest concentration in the plasma

TABLE 9

|  | Polymer weight ratio | Dose (mg/kg) | $T_{max}$ (hr) | $C_{max}$ (ng/mL) | $AUC_{last}$ (ng · hr/mL) |
| --- | --- | --- | --- | --- | --- |
| Example 6 | 1-fold amount | 10 | 2.0 ± 1.7 | 897 ± 579 | 4680 ± 3471 |
| Example 7 | 2-fold amount | 10 | 4.7 ± 3.1 | 1955 ± 706 | 11029 ± 2832 |
| Example 8 | 3-fold amount | 10 | 3.3 ± 1.2 | 3970 ± 2048 | 23859 ± 9799 |
| Example 10 | 4-fold amount | 10 | 2.7 ± 1.2 | 3262 ± 1065 | 17959 ± 3361 |
| Example 11 | 5-fold amount | 10 | 1.3 ± 0.6 | 3277 ± 604 | 18492 ± 4303 |
| Example 12 | 10-fold amount | 10 | 2.0 ± 0.0 | 3817 ± 551 | 22612 ± 1610 |

$AUC_{last}$: an area under the plasma concentration-time curve up to the final observation point

Test Example 5. Evaluation of an Amorphous State of the Solid Dispersion Containing the Compound A (Powder X-Ray Diffraction)

Since it is very important that the solid dispersion retains amorphous properties even after storage over time, the solid dispersions of Examples 9 to 11 were stored under open conditions at 40° C./75% RH, and a change in the amorphous state was evaluated using an X-ray diffraction device (D2 Phaser, Bruker). The results are shown in FIGS. 1 to 3.

($C_{max}$) and an area under the plasma concentration-time curve (AUC) were calculated from the change in the concentration in the obtained plasma. The results are shown in Table 10. Here, values in the table are the mean value±standard deviation of three examples.

When the solid dispersions of Examples 9 to 11 were stored under open conditions at 40° C./75% RH, decreases in the concentration in the plasma over time were not observed during storage for 7 weeks.

TABLE 10

|  | Dose (mg/kg) | Storage period | $T_{max}$ (hr) | $C_{max}$ (ng/mL) | $AUC_{last}$ (ng · hr/mL) |
| --- | --- | --- | --- | --- | --- |
| Example 9 | 10 | Before storage | 1.7 ± 0.6 | 3803 ± 679 | 32463 ± 15495 |
|  |  | 1 week | 3.3 ± 4.0 | 3559 ± 1240 | 18449 ± 4306 |
|  |  | 3 weeks | 2.7 ± 1.2 | 3265 ± 847 | 19633 ± 5698 |
|  |  | 7 weeks | 6.7 ± 2.3 | 3570 ± 939 | 15652 ± 5301 |
|  | 30 | Before storage | 4.0 ± 3.5 | 4132 ± 633 | 50613 ± 24625 |
|  |  | 1 week | 6.0 ± 3.5 | 5271 ± 431 | 37881 ± 8970 |
|  |  | 3 weeks | 4.7 ± 3.1 | 4760 ± 251 | 30196 ± 1575 |
|  |  | 7 weeks | 6.7 ± 2.3 | 6225 ± 1206 | 70629 ± 19727 |
| Example 10 | 10 | Before storage | 2.3 ± 1.5 | 2870 ± 863 | 23235 ± 4880 |
|  |  | 1 week | 2.3 ± 1.5 | 3650 ± 914 | 25137 ± 13623 |
|  |  | 3 weeks | 2.3 ± 1.5 | 3713 ± 1006 | 21674 ± 5359 |
|  |  | 7 weeks | 3.3 ± 1.2 | 3859 ± 748 | 21209 ± 3935 |

TABLE 10-continued

|  | Dose (mg/kg) | Storage period | $T_{max}$ (hr) | $C_{max}$ (ng/mL) | $AUC_{last}$ (ng · hr/mL) |
|---|---|---|---|---|---|
|  | 30 | Before storage | 2.7 ± 1.2 | 5798 ± 853 | 50798 ± 8981 |
|  |  | 1 week | 4.7 ± 3.1 | 6080 ± 1170 | 39819 ± 7414 |
|  |  | 3 weeks | 6.0 ± 3.5 | 4742 ± 990 | 29954 ± 7461 |
|  |  | 7 weeks | 4.0 ± 0.0 | 7704 ± 564 | 52920 ± 15388 |
| Example 11 | 10 | Before storage | 6.7 ± 2.3 | 2123 ± 303 | 21294 ± 11194 |
|  |  | 1 week | 2.3 ± 1.5 | 3217 ± 384 | 19802 ± 2229 |
|  |  | 3 weeks | 6.7 ± 2.3 | 3687 ± 158 | 19240 ± 9148 |
|  |  | 7 weeks | 2.7 ± 1.2 | 4833 ± 411 | 24934 ± 854 |
|  | 30 | Before storage | 2.7 ± 1.2 | 7557 ± 1529 | 74706 ± 40751 |
|  |  | 1 week | 3.3 ± 4.0 | 6002 ± 1522 | 29170 ± 10520 |
|  |  | 3 weeks | 2.0 ± 0.0 | 7504 ± 1978 | 48844 ± 4442 |
|  |  | 7 weeks | 4.0 ± 3.5 | 6624 ± 360 | 42405 ± 3280 |

$AUC_{last}$: an area under the plasma concentration-time curve up to the final observation point

Figure 4:
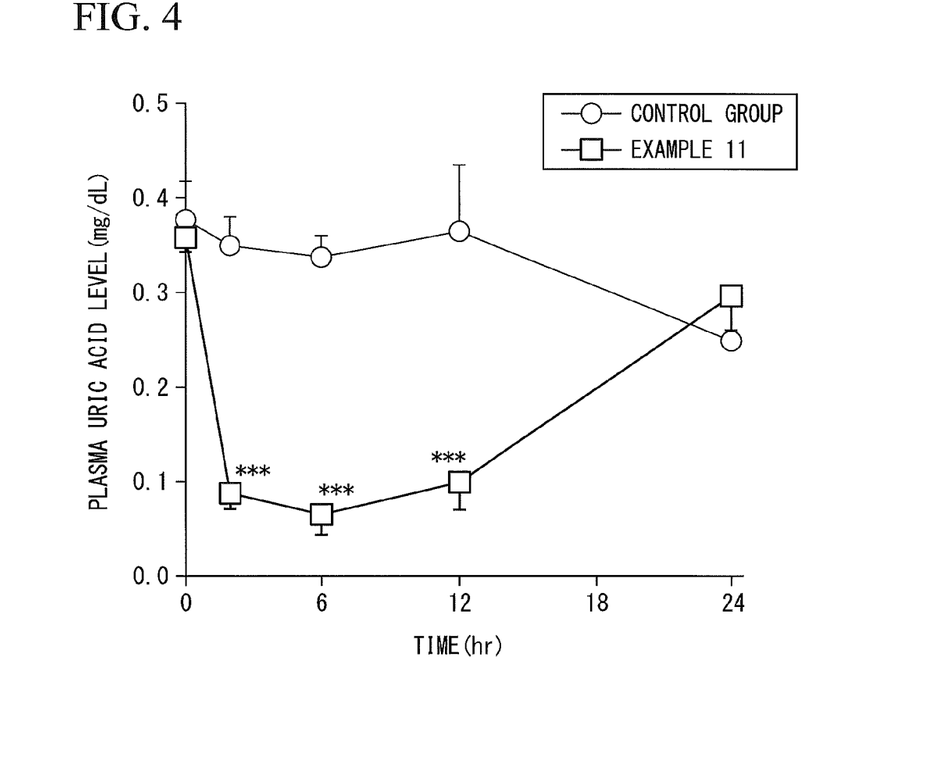
FIG. 4 is a graph showing an action of a solid dispersion of Example 11 lowering a plasma uric acid level in rats.

Test Example 7. Action of the Solid Dispersion Containing the Compound A Lowering a Plasma Uric Acid Level in Rats A single dose of 30 mg/kg, as the compound A, of the solid dispersion of Example 11 suspended in a 1% carboxymethylcellulose aqueous solution was orally administered to fasted male rats (8 weeks old, Crl:CD (SD), Japan Charles River Laboratories). A 1% carboxymethylcellulose aqueous solution was used as a control. A collection time was before administration (0), and 2, 6, 12, and 24 hours after administration, and about 300 μL of blood was collected at each time point from vena caudalis (n=5). The obtained blood was centrifuged at 1500×g, 4° C. for 15 minutes to obtain a plasma. A concentration of uric acid in the plasma was measured by HPLC (Hitachi High-Technologies Corporation). Welch's t-test was performed on plasma uric acid levels at each time point of the control group and Example 11. A level of significance was p<0.05 (both cases). The results are shown in FIG. 4.

The plasma uric acid level after the solid dispersion of Example 11 was administered was significantly lower than that of the control group, and the action of lowering a uric acid level was continuous.

Examples 13 and 14. Production of Solid Dispersions (HPMCAS-MG of 3-Fold Amount, and a Surfactant of 0.03-Fold Amount)

The compound A was dissolved in tetrahydrofuran and adjusted to 2.5 mg/mL. A HPMCAS-MG was dissolved in a mixed solvent (ethanol/water=4/1) and adjusted to about 45 mg/mL. Mixing was performed so that a weight ratio between the compound A, the polymer and the surfactant shown in Table 11 (polysorbate 80: Tween 80, sodium lauryl sulfate: SLS) was 1:3:0.03. Then, the mixture was pumped into a spray dryer (GB22, Yamato Scientific Co., Ltd.) at a rate of about 5 mL/min via a peristaltic pump, and spray drying and granulation were started from a 2-fluid nozzle (with a diameter of 406 or 508 μm) at an inlet temperature of 80° C. and an outlet temperature of about 60° C. under conditions of a dry air flow of 0.32 to 0.47 m³/min and a nozzle spray air pressure of 1.0 to 3.1 kgf/cm². The obtained primary dried component was additionally subjected to secondary drying (room temperature/overnight or room temperature/overnight at 40° C./day) using a vacuum pump and sieved (sieve opening: 300 μm).

TABLE 11

|  | Polymer Type | Polymer weight ratio Manufacturer | Surfactant | Surfactant weight ratio Manufacturer |
|---|---|---|---|---|
| Example 13 | HPMCAS MG | 3-fold amount Shin-Etsu Chemical Co., Ltd. | Tween 80 | 0.03-fold amount Tokyo Chemical Industry Co., Ltd. |
| Example 14 | HPMCAS MG | 3-fold amount Shin-Etsu Chemical Co., Ltd. | SLS | 0.03-fold amount KokusanChemical Co., Ltd. |

Test Example 8. Absorbability of the Solid Dispersion Containing the Compound A in Rats A single dose of 10 mg/kg, as the compound A, of the solid dispersions of Examples 13 and 14 suspended in a 1% carboxymethylcellulose aqueous solution was orally administered to fasted male rats (7-9 weeks old, Crl:CD (SD), Japan Charles River Laboratories). A collection time was 0.5, 1, 2, 4, 8, and 24 hours after administration, and about 300 μL of blood was collected at each time point from vena caudalis (n=3). The obtained blood was centrifuged at 1500×g, 4° C. for 15 minutes to obtain a plasma. The concentration of the compound A in the plasma was measured by HPLC (Shiseido and Hitachi High-Technologies Corporation). A time to reach the highest concentration in the plasma ($T_{max}$), the highest concentration in the plasma ($C_{max}$) and an area under the plasma concentration-time curve (AUC) were calculated from the change in the concentration in the obtained plasma. The results are shown in Table 12 together with Example 8. Here, values in the table are the mean value±standard deviation of three examples.

In the solid dispersions of Examples 13 and 14, differences were not observed in the concentration in the plasma compared to Example 8 containing no surfactant.

TABLE 12

|  | Polymer weight ratio/surfactant weight ratio | Dose (mg/kg) | $T_{max}$ (hr) | $C_{max}$ (ng/mL) | $AUC_{last}$ (ng · hr/mL) |
|---|---|---|---|---|---|
| Example 13 | 3-fold amount/ 0.03-fold amount | 10 | 3.3 ± 1.2 | 3625 ± 1335 | 21420 ± 4825 |
| Example 14 | 3-fold amount/ 0.03-fold amount | 10 | 2.7 ± 1.2 | 3589 ± 1370 | 21318 ± 6599 |
| Example 8 | 3-fold amount | 10 | 3.3 ± 1.2 | 3970 ± 2048 | 23859 ± 9799 |

Formulation Example 1

To 6.0 g of the solid dispersion obtainable in Example 5, 2.8 g of sodium carboxymethyl starch, 3.01 g of lactose, 2.1 g of hydrated silicon dioxide, and 0.1 g of magnesium stearate are added according to a conventional method, mixed together in a plastic bag, and the mixture is tableted using a rotary type tableting machine (VELA-5, Kikusui Seisakusho Ltd.) to produce a tablet.

Formulation Example 2

To 2 g of the solid dispersion obtainable in Example 5, 0.3 g of magnesium stearate and an appropriate amount of lactose are added to prepare a total amount of 23.5 g, which is mixed together in a plastic bag, and hand-filled in a No. 1 capsule to produce a capsule.

Formulation Example 3

To 1 g of the solid dispersion obtainable in Example 5, 16.0 g of lactose is added, stirred and mixed together in a plastic bag, the mixture is dried and granulated using a roller compactor (TF-MINI, Freund Corp), and particles are regulated using an oscillator (34-C-2, Kikusui Seisakusho Ltd.) to produce a granular agent.

INDUSTRIAL APPLICABILITY

The solid dispersion of the present invention is useful as a therapeutic agent for hyperuricemia and the like because it exhibits excellent in vivo absorbability and storage stability.

The invention claimed is:
1. A solid dispersion comprising a compound represented by General Formula (I):

(I)

wherein $R^1$ is an unsubstituted phenyl group or a phenyl group substituted with a substituent, the substituent being at least one group selected from the group consisting of an alkyl group having 1 to 8 carbon atoms, an alkyl group having 1 to 8 carbon atoms substituted with a halogen atom, an alkoxy group having 1 to 8 carbon atoms, an alkoxycarbonyl group having 2 to 8 carbon atoms, a formyl group, a carboxyl group, a halogen atom, a phenyl group and a phenoxy group, $R^2$ is a cyano group or a nitro group, $R^3$ is a hydroxyl group, X is an oxygen atom or $-S(O)_n-$, n is an integer of 0 to 2, and Y is an oxygen atom or a sulfur atom, or a pharmaceutically acceptable salt thereof and
a hypromellose derivative selected from hypromellose acetate succinate or hypromellose phthalate.

2. The solid dispersion according to claim 1, wherein $R^1$ is an unsubstituted phenyl group or a phenyl group substituted with a halogen atom.

3. The solid dispersion according to claim 1, wherein X is an oxygen atom.

4. The solid dispersion according to claim 1, wherein Y is a sulfur atom.

5. The solid dispersion according to claim 1, wherein the compound represented by General Formula (I) or a pharmaceutically acceptable salt thereof is amorphous.

6. The solid dispersion according to claim 1, wherein a weight ratio between the compound represented by General Formula (I) or a pharmaceutically acceptable salt thereof and a hypromellose derivative is 1:0.1 to 1:25.

7. A method of producing a solid dispersion, comprising: producing the solid dispersion according to claim 1 using a spray dry method.

8. A pharmaceutical composition comprising the solid dispersion according to claim 1.

9. The pharmaceutical composition according to claim 8, which is a solid preparation.

10. The solid dispersion according to claim 1, wherein the hypromellose derivative is hypromellose acetate succinate in which a substitution proportion per monomer unit is 21 to 25% for a methoxy group, is 5 to 9% for a hydroxypropoxyl group, is 7 to 11% for an acetyl group, and is 10 to 14% for a succinoyl group.

11. The solid dispersion according to claim 10, wherein the compound represented by General Formula (I) is 2-(3-cyano-4-phenoxyphenyl)-7-hydroxythiazolo[5,4-d]pyrimidine.

12. The solid dispersion according to claim 11, wherein a weight ratio between the compound represented by General Formula (I) or a pharmaceutically acceptable salt thereof and the hypromellose derivative is 1:2 to 1:5.

13. The solid dispersion according to claim 12, wherein the weight ratio between the compound represented by General Formula (I) or a pharmaceutically acceptable salt thereof and the hypromellose derivative is 1:3 to 1:4.

14. A method of producing a solid dispersion according to claim 1 by a solvent method using one or more solvents selected from the group consisting of ethanol, methanol, 2-propanol, acetone, 2-butanone, methyl isobutyl ketone, tetrahydrofuran (THF), tetrahydropyran, 1,4-dioxane, diethyl ether, toluene, acetonitrile, methylene chloride, chloroform, methyl acetate, ethyl acetate, butyl acetate, acetic acid, formic acid, N,N-dimethylformamide, N,N-dimethylacetamide, and dimethyl sulfoxide.

* * * * *